United States Patent [19]
Beljanski

[11] Patent Number: 5,413,787
[45] Date of Patent: May 9, 1995

[54] BIOPARYL, A BIOLOGICAL REGULATOR, ACTIVE AGAINST VARIOUS PATHOLOGIES

[76] Inventor: Mirko Beljanski, 46, Blvd. de Port Royal, 75008 Paris, France

[21] Appl. No.: 365,045

[22] Filed: Jun. 9, 1989

[30] Foreign Application Priority Data

Jul. 19, 1988 [FR] France ................. 88 09738
Apr. 26, 1989 [EP] European Pat. Off. .......... 89401191

[51] Int. Cl.⁶ .............................................. A61K 35/78
[52] U.S. Cl. .................................................. 424/115.1
[58] Field of Search .............. 424/195.1; 514/464; 560/249

[56] References Cited

U.S. PATENT DOCUMENTS 4,537,774  8/1985  Shimizu et al. ............... 424/195.1
4,571,407  2/1986  Chatterjee et al. ............ 514/464
4,886,904  12/1989  Tanaka et al. ................. 560/249

OTHER PUBLICATIONS

Nakanishi, "The Ginkgolides", *Pure and Applied Chemistry*, 14, pp. 89–113 (1983).

*Primary Examiner*—Jill A. Warden
*Assistant Examiner*—S. G. Marshall
*Attorney, Agent, or Firm*—Roland Plottel

[57] ABSTRACT

Bioparyl is obtainable by a disclosed extraction hydrolysis and purification procedure applied to golden autumn leaves of the *Gingko biloba* tree. Bioparyl plays an important role in the regulation of the activity of certain enzymes, particularly ribonucleases (RNases), implicated in the fundamental mechanism of gene expression. It is low in or free from toxic or side effects in healthy animals, and can be used to ameliorate several pathogenic conditions. Bioparyl is effective in preventing or reversing fibrosis in various tissues, including the lungs and skin, engendered by radiation or chemotherapy. It reduces abnormally high concentrations of gamma-globulins and immuno-globulins found in certain inflammatory or auto-immune diseases, including Acquired Immune Deficiency Syndrome disease (AIDS). In patients with leukemia or solid cancers, Bioparyl normalizes the activity of ribonucleases.

7 Claims, 13 Drawing Sheets

TABLE I Example I : patients affected by auto-immune deseases

| Days | Immunoglobulins (IgM) gramme / liter | |
|---|---|---|
| | Patient A | Patient B |
| d-0 | 5 | 9 (N= 0.65-2.10) |
| Bioparyl | | |
| d-40 | 2 | - |
| d-60 | - | 3 |

Example II : AIDS positive patient before and after treatment by Bioparyl

| Days | γ-globulins level (%) | level of IgG (%) | level of albumen (%) |
|---|---|---|---|
| d-0 | 27.7 (N=12-18) | 24.5 (N=7-14) | 49 (N=52-60) |
| Bioparyl | | | |
| d-15 | 21 | 21.8 | 62 |
| d-25 | 20 | 19.5 | 60 |

TABLE II

Survival of ♂ Swiss mice bearing Ehrlich ascitic cells and treated by Bioparyl

| Survival (days) | untreated mice | mice treated by Bioparyl |
|---|---|---|
| 0 | 10/10 | 10/10 |
| 21 | 0/10 | 6/10 |
| 60 | — | 4/10 |
| 90 | — | 4/10 |

Bioparyl : 2 x 3 mg/day, during 8 consecutive days (i.p. route)

Survival of ♀ Swiss mice bearing Ehrlich ascitic cells and treated by Bioparyl

| Survival (days) | untreated mice | mice treated by Bioparyl |
|---|---|---|
| 0 | 10/10 | 10/10 |
| 24 | 0/10 | 7/10 |
| 60 | — | 5/10 |
| 90 | — | 5/10 |

Bioparyl : 2 x 3 mg/day, during 8 consecutive days (i.p. route)

FIG. 11

TABLE III

Survival of ♂ BALB C mice bearing lymphoma YC8 cells and treated by Bioparyl

| Survival (days) | untreated mice | mice treated by Bioparyl |
|---|---|---|
| 0 | 10/10 | 10/10 |
| 25 | 4/10 | 10/10 |
| 30 | 0/10 | 5/10 |
| 60 | — | 5/10 |
| 90 | — | 5/10 |

Bioparyl (2 x 3 mg/day during 8 consecutive days (i.p. route)

Survival of ♀ BALB C mice bearing lymphoma YC8 cells and treated by Bioparyl

| Survival (days) | untreated mice | mice treated by Bioparyl |
|---|---|---|
| 0 | 10/10 | 10/10 |
| 24 | 3/10 | 9/10 |
| 30 | 0/10 | 8/10 |
| 60 | — | 5/10 |
| 90 | — | 5/10 |

Bioparyl (2 x 3 mg/day, during 8 consecutive days (i.p. route)

FIG. 12

BIOPARYL, A BIOLOGICAL REGULATOR, ACTIVE AGAINST VARIOUS PATHOLOGIES

BACKGROUND OF INVENTION

For the maintenance, and also for the division of cells, it is necessary for the cell to reproduce its genome (DNA), then to transcribe the genes (DNA) into various RNAs among which are messenger RNAs, which in turn direct the synthesis of proteins. The biological medium that permits this is extremely complex. Various enzymes are present in the biological system to carry out these and other cellular functions.

Conditions leading to a pathological situation may result from alterations or degradations of elements in one or another of these steps. Endogenous or exogenous factors can affect the events of these various steps. Conversely, pathological states may be ameliorated by introducing into the biological system suitable entities that act directly or indirectly (but always in a selective fashion) on DNA, RNA and/or enzymes.

BRIEF DESCRIPTION OF THE INVENTION

A standardized material has been produced and named "Bioparyl". It plays an important role in the regulation of the activities of certain enzymes, particularly ribonucleases (RNases), but also others, implicated in the fundamental mechanisms of gene function. Bioparyl acts at different cellular levels, always in a selective manner on what is pathological, deregulated enzymes, DNA or RNA of damaged or cancerous cells. Its mode of preparation is original as well as its fields of application.

Bioparyl is obtainable from golden leaves of the Gingko biloba tree, collected at the end of the autumn. A standardized method of preparation comprises several steps: extracting the active principle present in the leaves with wager, preferably hot; optionally, concentrating the extract by evaporating part of the water; doing an acid-hydrolysis; partially neutralizing; centrifuging and recovering the supernatant; fractioning on a chromatography column, eluting with water.

Bioparyl is substantially devoid of toxic or secondary effects, at cellular level as well as in animals. It can be used during long periods in order to ameliorate various pathologies. It has no effect on arterial tension, which is as usually found with other preparations made by other methods from leaves of the same tree.

Bioparyl is very effective for treatment or prevention of fibrosis of various tissues or organs, e.g. lungs, skin, resulting either without known causes or resulting from different treatments, e.g. radiation, drugs. It is capable of reversing or curing fibrosis already induced by these agents. For example, a patient suffering from lung cancer may be subjected to radiation and/or chemotherapy, e.g. with Bleomycin, and simultaneously to treatment with Bioparyl.

Bioparyl possesses a certain specific effect against tumor cells. Bioparyl also normalizes the level of gamma-globulines and/or immuno-globulines which are too high, accumulated during certain inflammatory diseases, auto-immune diseases or viral diseases, including Acquired Immune Deficiency Syndrome (AIDS).

In patients having malignant diseases (solid cancers, blood or lymph cancers), one detects almost always a quantitative or qualitative abnormality of ribonucleases (RNases) activity. Bioparyl normalizes the function and the amount of these enzymes, which has as a consequence to ameliorate the general state of patients or to prevent or even to stop the appearance of necessary elements for development of the pathology. In leukemia patients, Bioparyl may be used to slow down the formation of blasts.

Bioparyl may contain one or more than one active chemical entity, and its different physiological effects may be attributable to one or to different such entities. It is my intent that the term "Bioparyl" covers both the extract and any active individual chemical entities therein.

DETAILED DESCRIPTION OF THE INVENTION

Method for preparation of Bioparyl from Gingko biloba golden-autumn leaves

In the autumn, just at the moment of their fall, golden leaves are collected from the Gingko (also sometimes spelled Ginkgo) biloba tree. The leaves may then either be frozen or dried.

Five to seven k of frozen leaves (or about 2.5–3 kg of dried leaves) are covered with tap water (about 7–8 liters) and boiled for three hours. Liquid is removed and concentrated by distillation to about 1 liter. (A second ebullition of leaves is achieved, the liquid being used for the next first ebullition of another batch of leaves).

To one liter of concentrated liquid, hydrochloric acid is added to a final concentration of 1N. The mixture is then hydrolysed for 30 minutes at 100° C. When the temperature has cooled to about 50° C., the pH is adjusted to about 3–4 (by addition of KOH or NaOH). A fast centrifugation (5–7 min. at 6,000 rpm) is carried out. An important quantity of hydrolysed and insoluble material is thus eliminated. Only the supernatant (brown-red liquid) is saved (the pellet is discarded). This liquid is either used directly or frozen. It is called ZAC.

200–300 grams of ZAC (dry-weight determined on 0.5 ml sample), constituting about 300–400 milliliters, are settled on the top of a 70 cm×7 cm column containing Sephadex G-25 fine, swelled and equilibrated in advance with de-mineralized water. Elution is carried out with de-mineralized water from the beginning of the elution to the end of the white-yellow part (very fluorescent as can be seen with UV light); eluates are collected together and concentrated either by distillation or by ebullition under compressed air, which is a rapid way. When eluate is concentrated to about 1 liter, the pH is adjusted to about 7.0, and the amount of material is determined by weighing the dry-weight of an aliquot part.

Total weight in grams divided by 30 will give the number of patients capable of utilizing, during 30 days (1 month), 1 g Bioparyl/day (2×0.5 g). This number of patients is "A".

The liquid is then concentrated again to about 500 ml, mixed with cellulose powder (Whatman CF1) and then dried in an oven at 60°–80° C. for several hours. The material is hand mixed from time to time in order to avoid agglomeration. Once dried, the powder is milled and weighed. Total weight divided by the number A gives the amount of powder (Bioparyl+cellulose) to be settled in 60 capsules for 1 month treatment (2 capsules per day, which correspond to 2×0.5 g of Bioparyl/day).

Eluate of the column, concentrated to 500 ml (pH 7.0) is a water solution of Bioparyl. This Bioparyl, prepared according to the above-described method, was used in all experiments described below. However, the preparation was first diluted 5 times with distilled water, centrifuged at 10000 rpm for 10 min. and filtered on millipore filters before it was again weighed.

The analysis of compounds found in Gingko biloba leaves has been studied by several authors. However, the method of preparation, as well as the applications of Bioparyl, differ entirely: it differs by the choice of material (golden and not green leaves), by liquid used for extraction (here water and not organic solvents as always used as described in the literature), by hydrolysis, which eliminates a large number of undesirable substances by centrifugation after pH has been adjusted, and which again eliminates by selection on the column. In fact, here again an important part of initial material is eliminated from what will constitute the "Bioparyl".: when Sephadex column is washed with diluted alkali and afterwards with water until pH becomes neutral, one observes that an important part of the material was retained on the column. Once washed, the column may serve again.

Green leaves extracts of Gingko biloba are commercially available as "standardized preparations". They contain substances which are not present in Bioparyl and are recommended to obtain modifications of arterial, capillary or venous circulation, or to improve brain circulation. All these preparations, which are prepared by very different routes, exhibit contra-indications which do not exist in Bioparyl. Bioparyl at much higher dosages (up to 2 g/day during weeks) has not permitted to detect even a slight undesirable variation or alteration of patient's condition.

The difficulty to analyze the various compounds present in leaves of the Gingko biloba tree is well known. Many pharmaceutical companies have tried without success and consequently sell "standardized composition". For this reason, we insist very particularly on the fact that our technique for standardized preparation totally differs from that used by other pharmaceutical companies and that the applications are also totally different. This is very important since there are no other actual methods used for struggle against fibrosis, or to regulate RNases activities and modulate the immuno-globulins in the plasma of diseased patients. Moreover, our preparations do not exhibit undesirable side effects. Bioparyl possesses also an anti-cancer effect which, although insufficient, nonetheless contributes in maintaining and recovering a healthy condition in animals bearing cancers.

EXAMPLE 1

Effect of Bioparyl on RNases

Persons affected by various cancers usually present abnormalities in the activity of their plasmatic RNases. Bioparyl possesses a strong regulatory effect in vitro and in vivo; that is to say, it brings back close to normal values the activities of RNases from cancer patients' plasma. In function of time, a patient regularly taking Bioparyl normalizes the activity of his ribonucleases; the effect is maintained after Bioparyl treatment has been suspended.

Peripheral blood is taken on sodium citrate (10 mg for 5 ml of blood), in order to avoid blood coagulation without interfering with enzymes' activities. After centrifugation, the plasma is carefully taken off and serves as a source of RNases. The plasma is used after 10-fold dilution with Tris-HCl buffer $10^{-3}$ M pH 7.60, and the amount of proteins is determined (Biuret reaction).

Bioparyl dissolved in distilled water (pH 7.0, 5 mg/ml) is used (0.01 to 0.05 ml). Incubation medium (0.15 ml final volume) contains: Tris-HCl buffer, $10^{-2}$ M pH 7.60: 0.05 ml; $^3$H-RNA (r-RNA or 4 S RNA), 100 μg, 15,000 CPM: 0.05 ml; ten-times diluted plasma: 0.01 to 0.05 ml. After incubation at 36° C. for 10 min. (water bath) (generally necessary conditions but that may vary in case of necessity), the reaction is stopped by addition of 3 ml trichloroacetic acid (TCA) (5%); the tubes are cooled in order to assure a good precipitation of proteins and undegraded $^3$H-RNA.

The precipitate is filtered on glass millipore (GF/C, Whatman), washed with 5% TCA solution then with 95° ethyl alcohol. The filters are dried and the radioactivity determined in a scintillation spectrometer. The results are expressed as percent of non-degraded radioactive RNA, the radioactivity of initial intact RNA being taken as 100%.

Figure 1A:
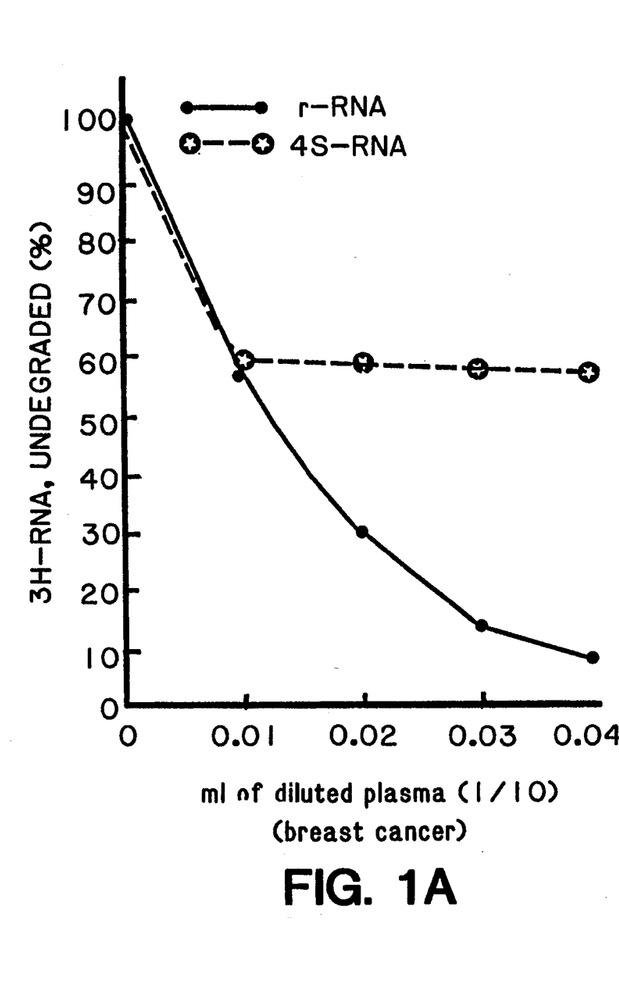
FIG. 1. In vitro activity of RNases in plasma of healthy or cancer persons, on radioactive ribosomal RNA (r-RNA) and radioactive transfer RNA (4 S RNA).
Figure 1B:
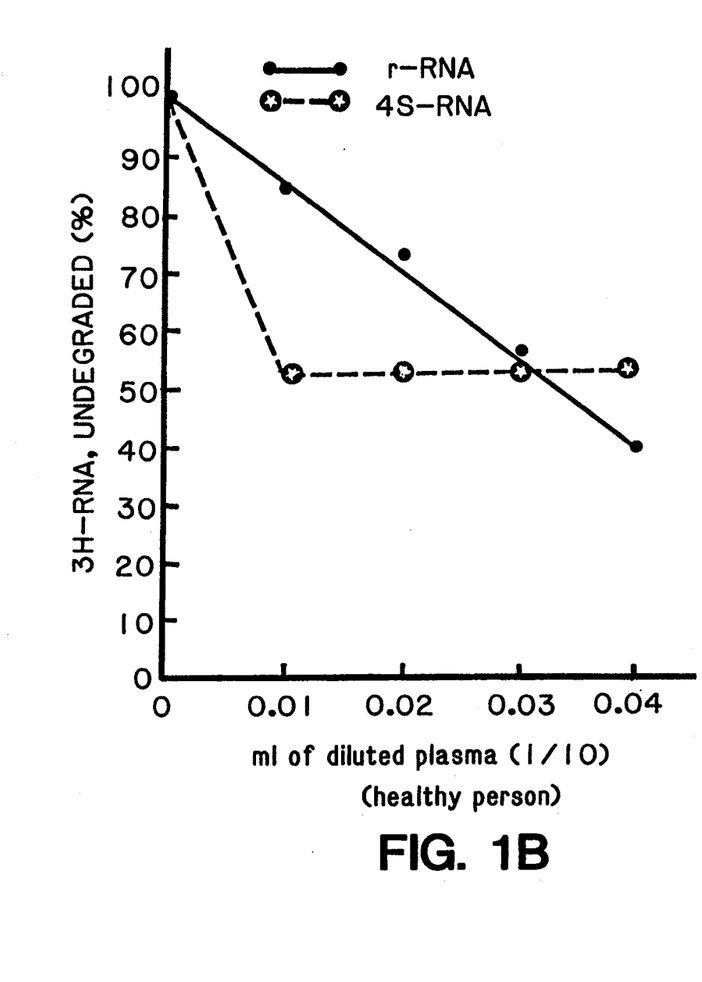
Figure 2A:
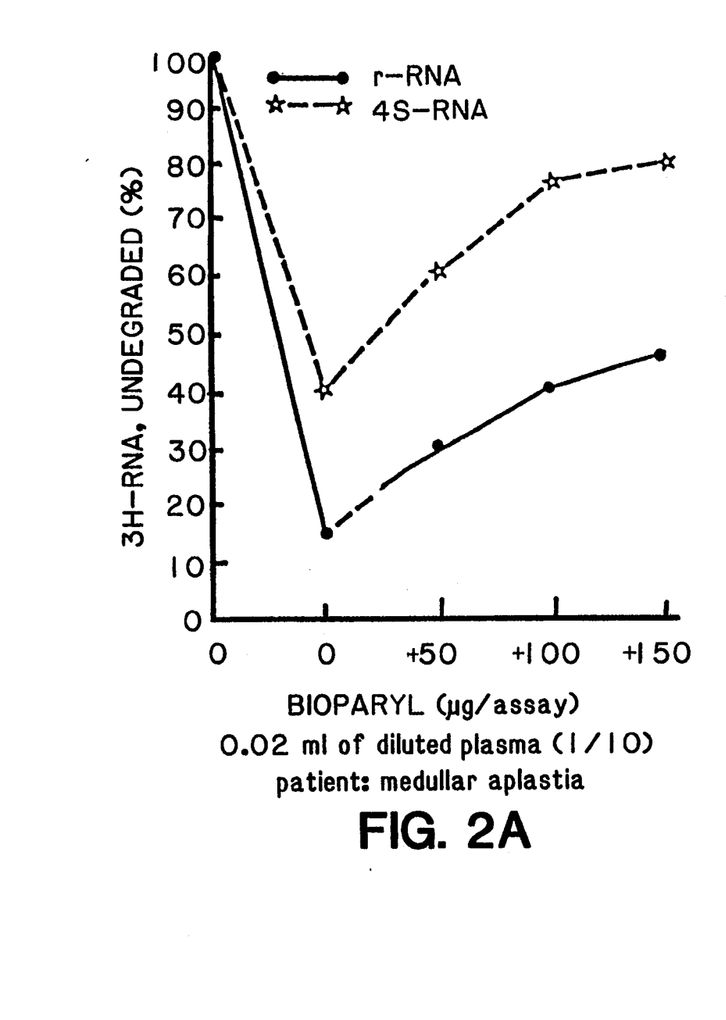
FIGS. 2 and 3. Effect of Bioparyl on the activities of RNases in plasma of patients carrying different pathologies.
Figure 2B:
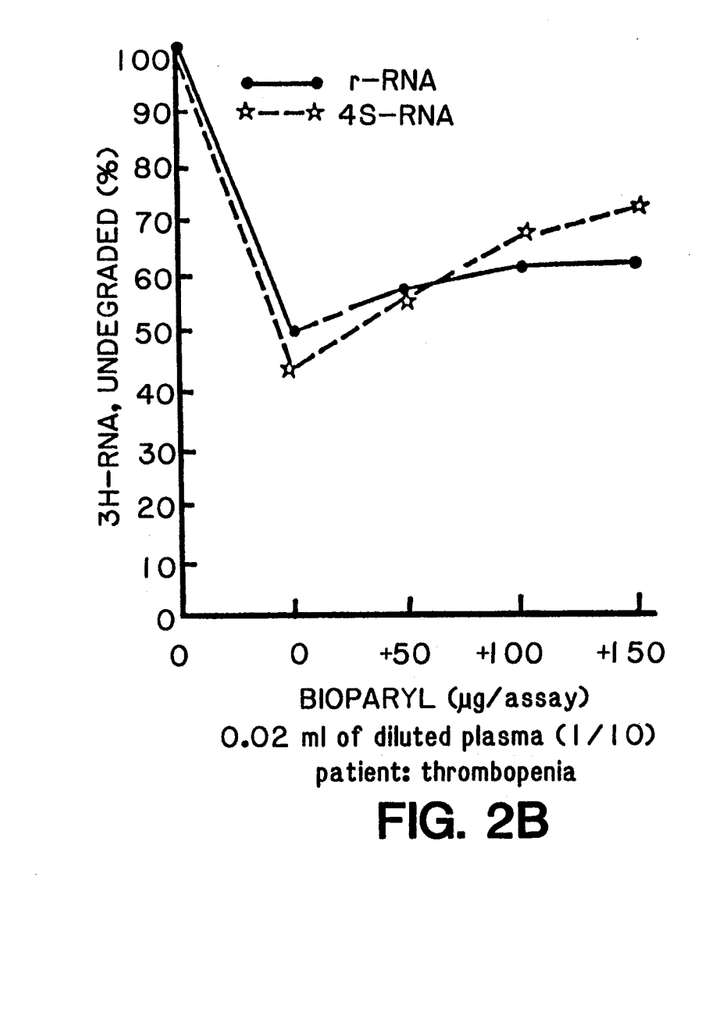
Figure 2C:
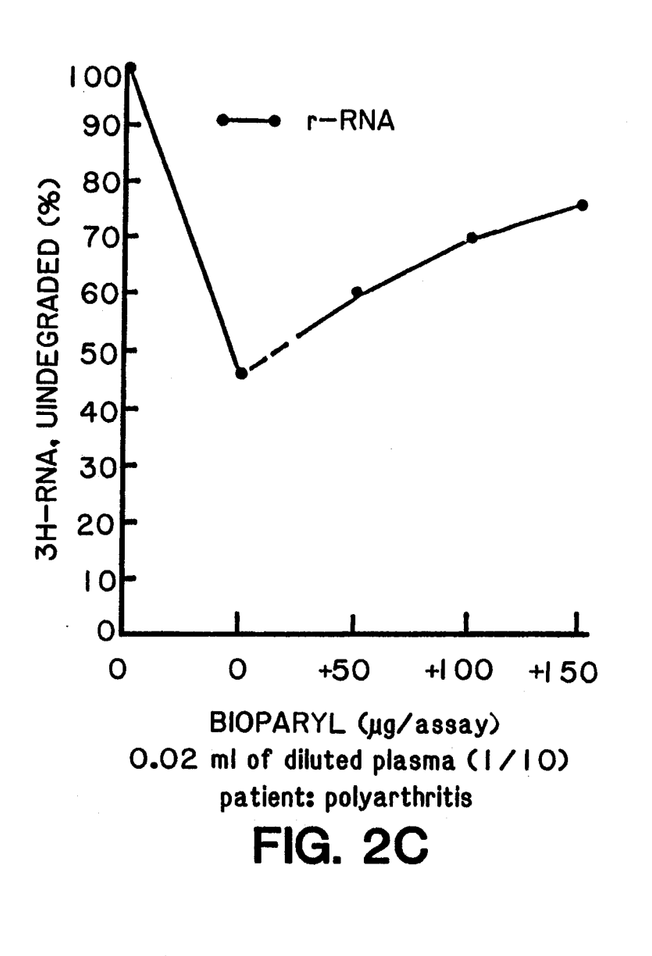
Figure 2D:
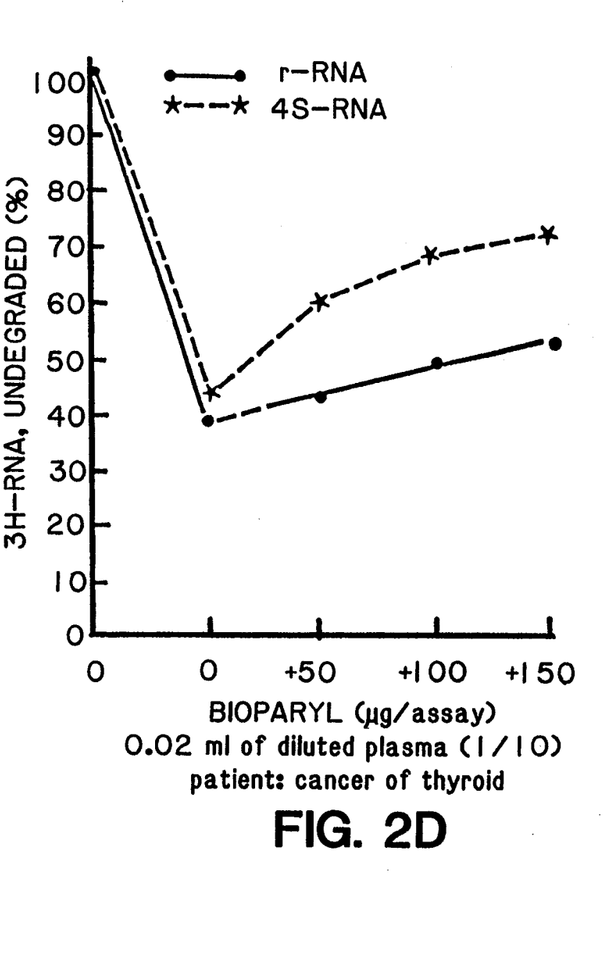

FIG. 1 shows that RNase in the plasma of a patient affected by a breast cancer strongly degrades r-RNA (long chain RNA) while such a degradation is not observed with 4 S RNA (short chain RNA). On FIG. 1, one sees that enzyme from a healthy person degrades long chain RNA much less than in the case of the cancer patient.

In general, the activities of RNases from patients affected by cancers are strongly increased, which stimulates the catabolism, weakens the patient and also participates in the maintenance of the cancerous state. As far as is known at the present time, one cannot say if this increase of RNase activity is due to a much higher amount of these enzymes (overactivation of corresponding genes) or to the presence of a metal, for example, accelerating these activities.

Figure 3A:
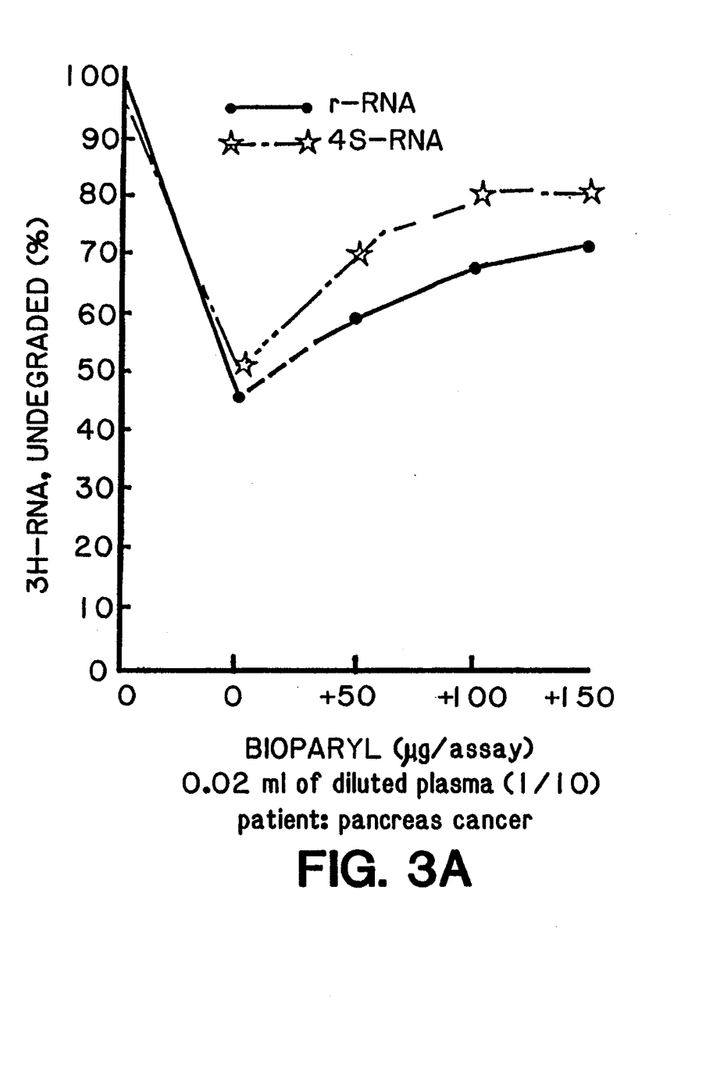
Figure 3B:
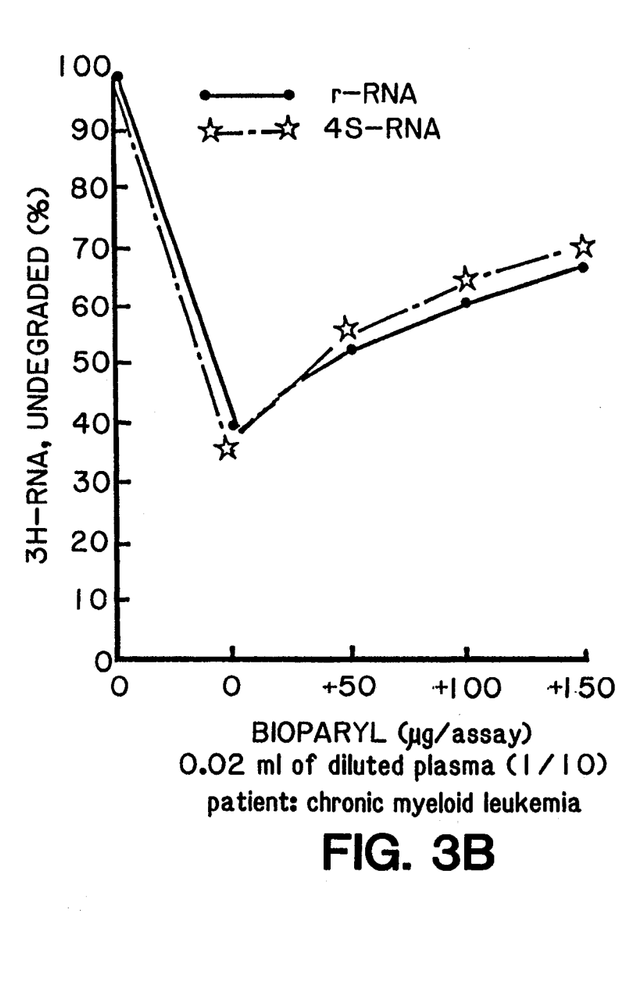
Figure 4:
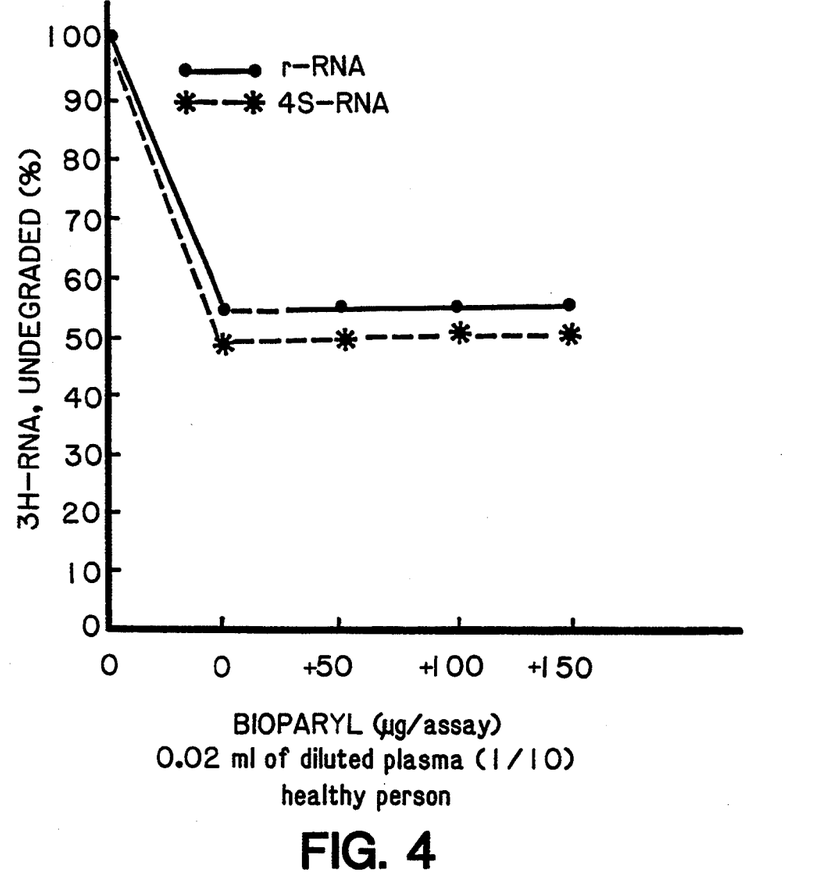
FIG. 4. Absence of effect of Bioparyl on RNases in plasma of healthy people.

Bioparyl inhibits in vitro the activity of RNases which are too much active in plasma of persons affected by diseases (FIGS. 2 and 3), but has no effect on those RNases coming from plasma of healthy persons (FIG. 4). This indicates either that enzymes are different, or that there exist particular co-factors allowing this selective action of Bioparyl, which is an extremely important phenomenon.

EXAMPLE 2

Effect of iron and Bioparyl on in vitro activities of RNases

Figure 5:
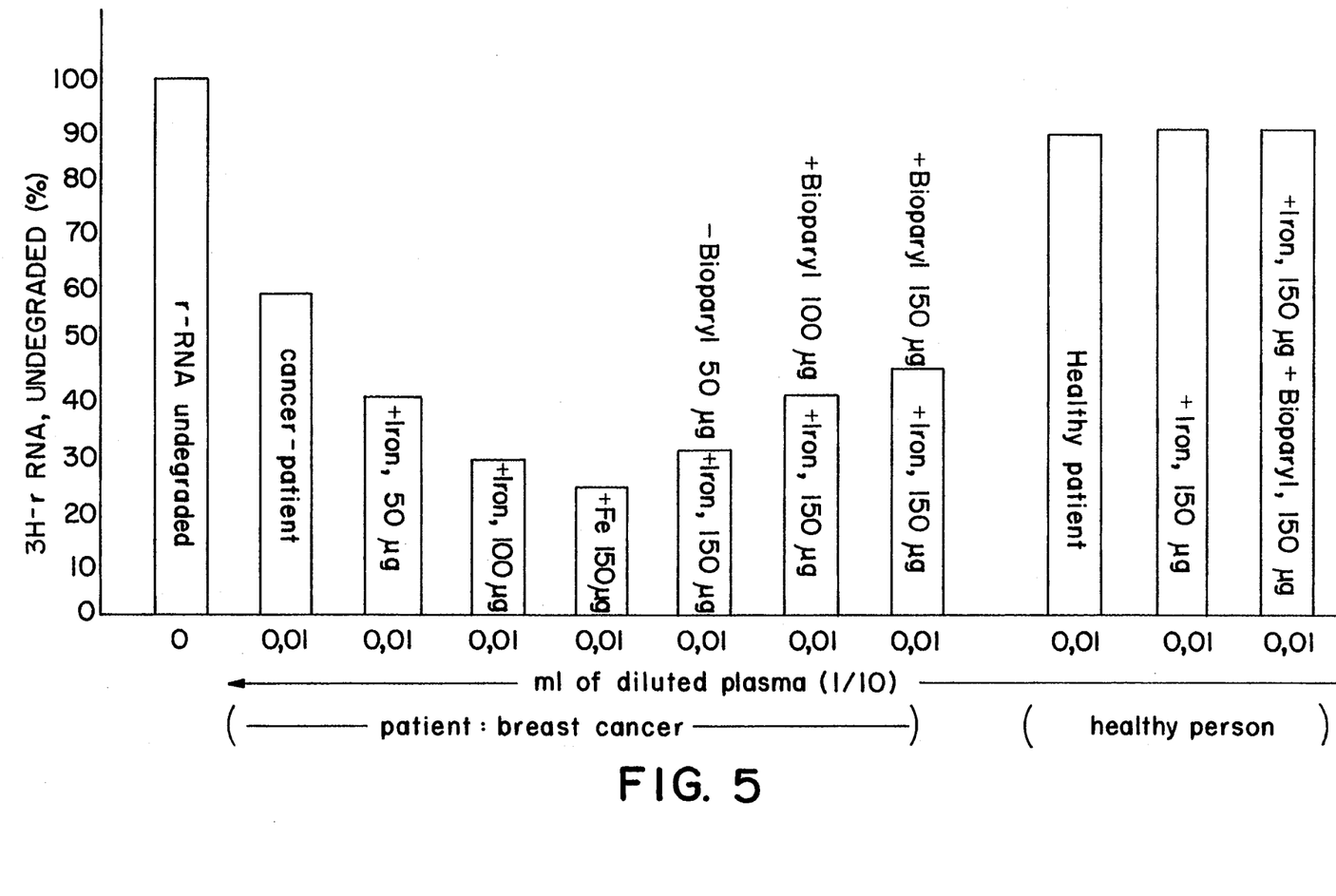
FIG. 5. Effect of iron on the activity of RNases of a person having cancer and of a healthy person. Effect of Bioparyl.

Ferric iron strongly accelerates the in vitro activity of RNases from patients affected by cancers (leukemia, solid cancers, liver in particular), or auto-immune diseases (polyarthritis, thrombopenia) and in certain viral pathologies, AIDS for example. But the iron is without effect on the in vitro activity of RNases which are found in plasma of healthy persons (FIG. 5). One knows that the RNases enable the furnishing of the RNA primers necessary for the replication of DNA, and that the primers accepted by DNA from healthy tissues are not the same as the primers required for replication of DNA from cancer tissues. Thus, regulation of RNases (enzymes able to provide primers in cells)is a capital phenomenon in carcinology and virology.

By its capacity to regulate what is deregulated, and only that, even in the presence of iron, Bioparyl is an extremely important and innovative agent for normalization.

EXAMPLE 3

Figure 6A:
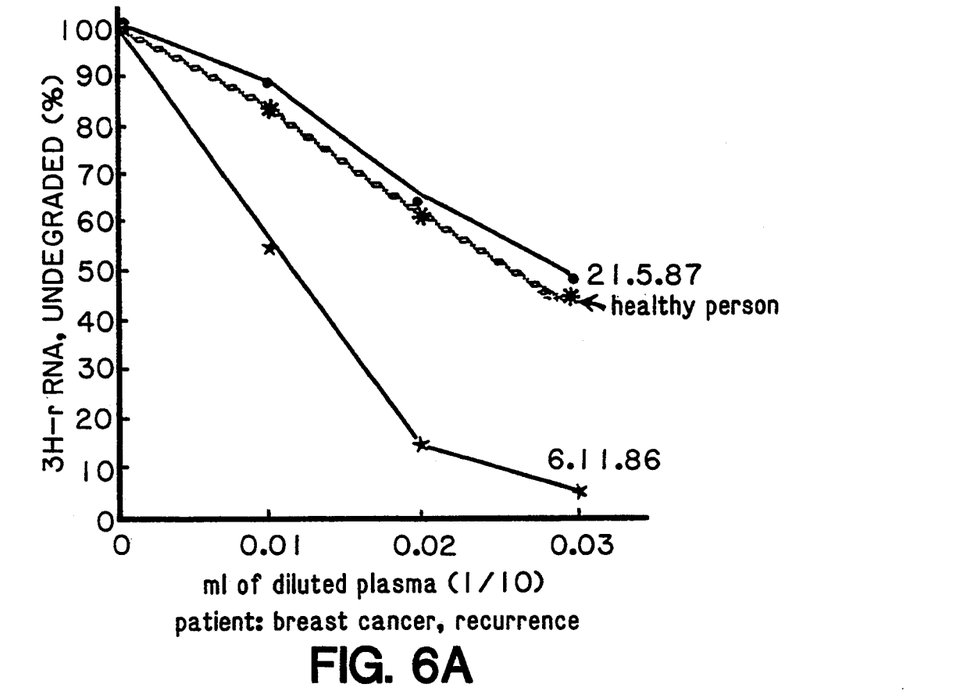
FIG. 6. Normalizing effect of Bioparyl on plasma RNases from persons having cancers.
Figure 6B:
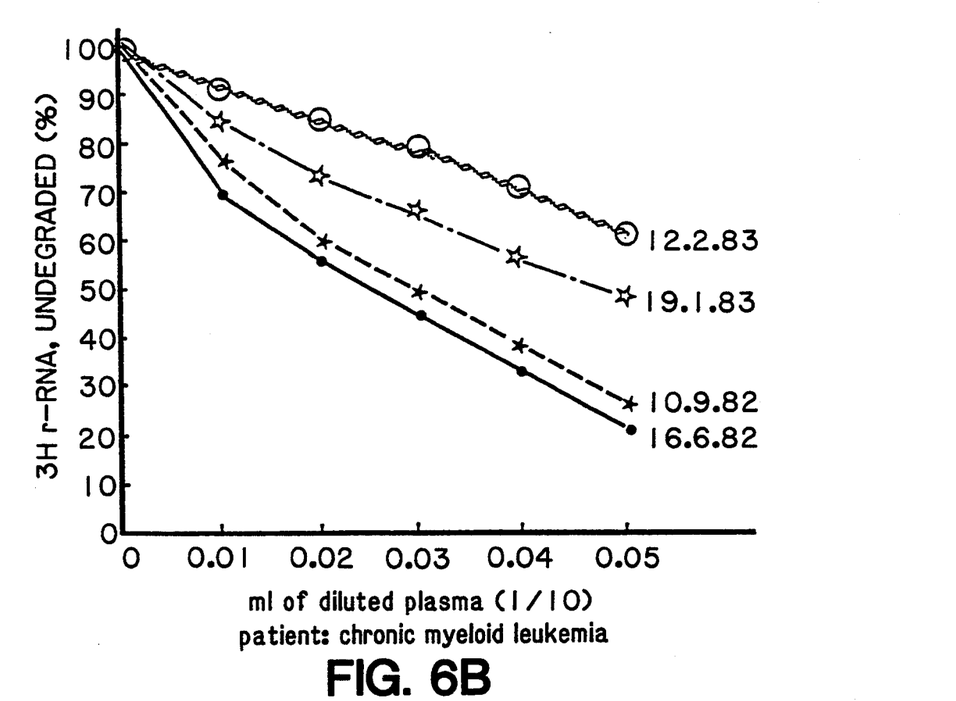

Normalization in vivo of plasma RNases of a patient affected by a cancer and regularly using Bioparyl In the case of solid cancers or leukemic patients (in particular those patients affected by myeloid chronic leukemia), undergoing chemotherapy or not, Bioparyl, administered orally (1 g/day each day) corrects over a period of time the disturbed activity of RNases in the circulating blood, and brings their values closer to those observed in healthy persons. FIG. 6 shows, in function of time, this normalization of the activity of RNases in plasma from patients affected by two different types of cancer (treatment was arrested 3 days before each blood sample was taken).

EXAMPLE 4

Radiation fibrosis. In vitro studies

Figure 7A:
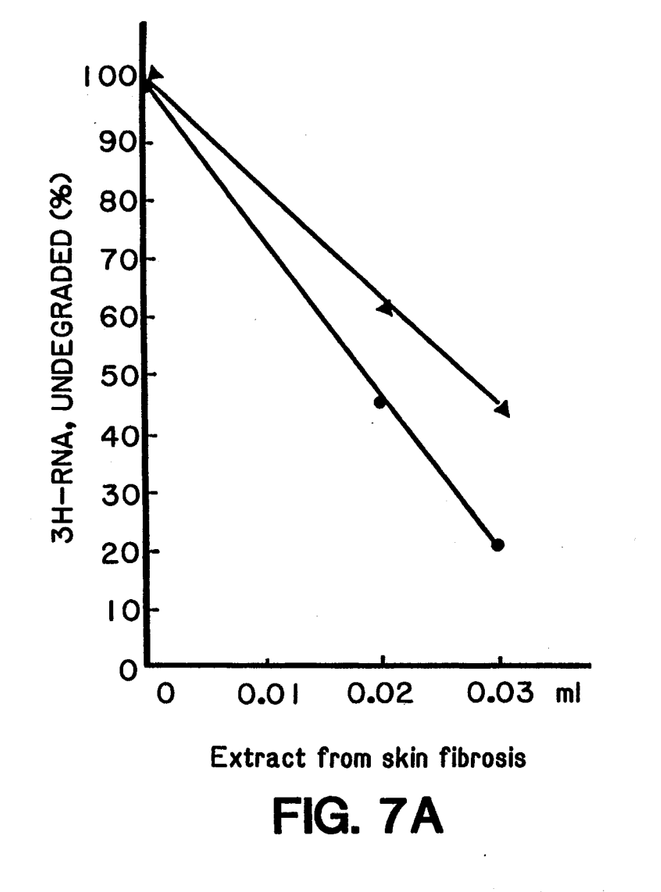
FIG. 7. Activity of RNases from human fibrosis skin Effect of iron and Bioparyl.
Figure 7B:
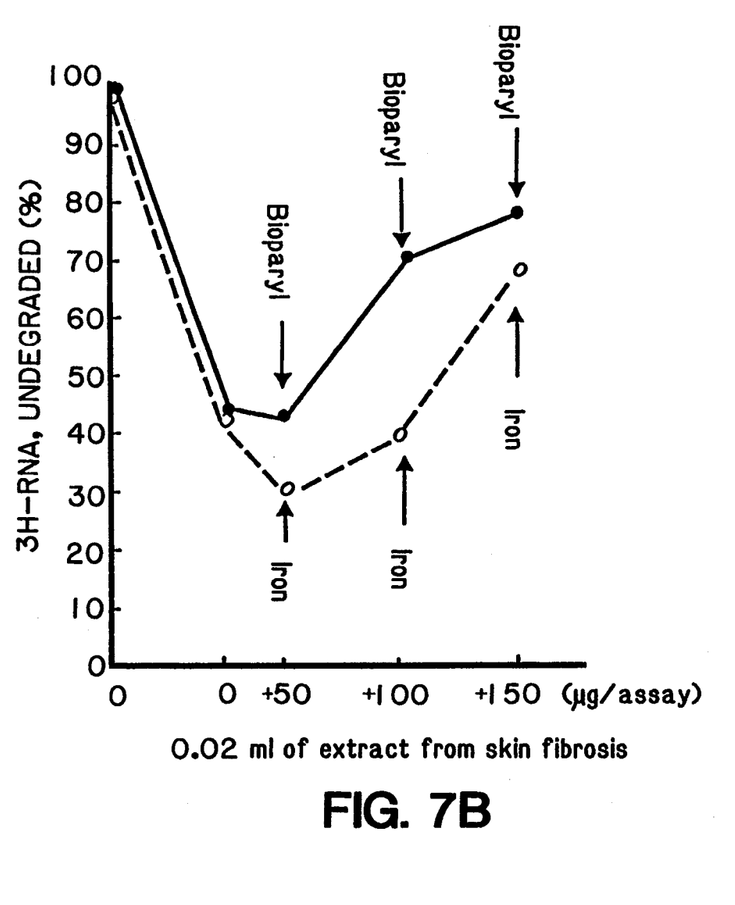

Sample of skin fibrosis induced by radiation has been broken in a mortar (4° C.) in the presence of Tris-HCl buffer 0.02M containing 0.06M KCl and 0.001M $MgCl_2$. Final volume: 1.5 ml. The activity of RNases present in this extract has been tested with 4 S RNA and ribosomal RNA (r-RNA); 0.01; 0.02; 0.03 and 0.04 ml of enzyme extract were incubated in the presence of radioactive $^3$H-r-RNA or $^3$H-4 S RNA. Incubation time: 15 min. at 36° C. The results are illustrated in FIG. 7. Degradation of labelled RNA is linear in function of increasing concentration of the extract. r-RNA is more rapidly degraded than 4 S RNA. Bioparyl strongly inhibits, but not completely, the degradation of r-RNA. Ferric iron ($FeCl_3$), at low concentrations, stimulates r-RNA degradation; but at higher concentrations it inhibits it. For ethical reasons, we did not use normal human skin. However, Bioparyl does not act on RNase from normal skin of a young lamb.

Effect of Bioparyl on skin DNA. Bioparyl stimulates the in vitro synthesis of DNA from healthy skin of young lamb as well as that of DNA isolated from the healthy skin of young mice.

Figure 8:
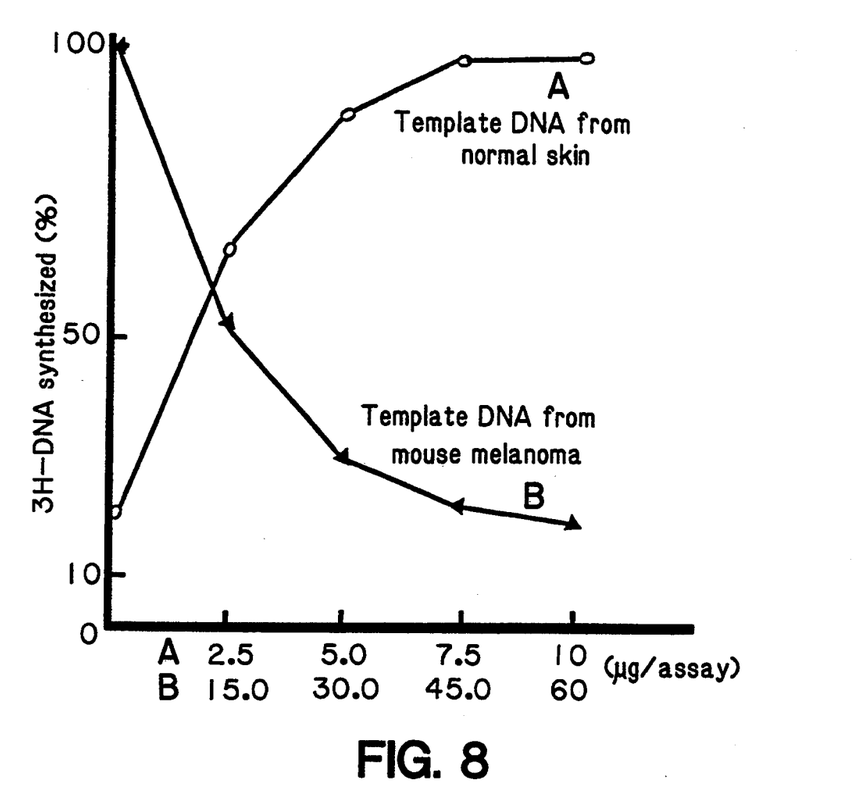
FIG. 8. Stimulation by Bioparyl of the in vitro normal skin DNA synthesis. Beautiful inhibiting action on that of melanoma.

DNA from healthy skin of young animals has been isolated by the procedure described in Experimental Cell Biol. 49:220-231 (1981) which also gives the method used for DNA in vitro synthesis. FIG. 8 shows that Bioparyl strongly stimulates the replication of DNA from healthy skin. It is remarkable to observe a very beautiful inhibition of the synthesis of DNA isolated from mice melanoma B 16 F 10, kindly supplied by Mrs. Poupon, Institut Gustave Roussy.

Effect in vivo of Bioparyl on fibrosis

Post-irradiation lesions have been treated by Bioparyl in patients having undergone radiotherapy. Oral dosage was 0.5 g×2/day during several weeks. The efficacy is certain, particularly for skin or mucous membrane fibrosis. One obtains 83% objective responses for post radiation cutaneous-mucous fibrosis. Pericardite fibrosis may also be efficiently cured by Bioparyl. When fibrosis dates less than 1 year, 71% of objective responses are obtained. Dose-effect ratio has not yet been determined.

EXAMPLE 5

Bioparyl corrects high amount of immuno-globulins in patients bearing AIDS virus or affected by auto-immune disease Certain pathologies (AIDS, polyarthritis, sclerosis or other diseases) induce abnormally high amounts of various immuno-g10bulins (IgM, IgG, etc.) which is harmful to immunological equilibrium. The use of Bioparyl by oral route (1 g/day every day) permits one to observe in 3-5 weeks of treatment a decrease of globulins amount. One observes immediate clinical amelioration which continues during treatment by Bioparyl. Results are illustrated in Table I.

EXAMPLE 6

Inhibition of synthesis of DNA of cancer cells

Figure 9A:
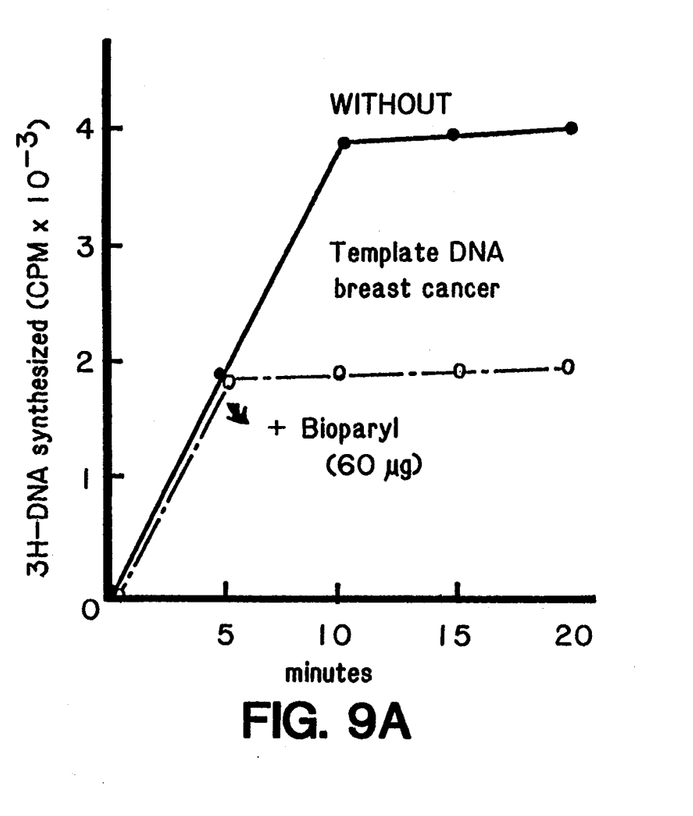
FIG. 9. Inhibition of synthesis of DNA of cancer cells.
Figure 9B:
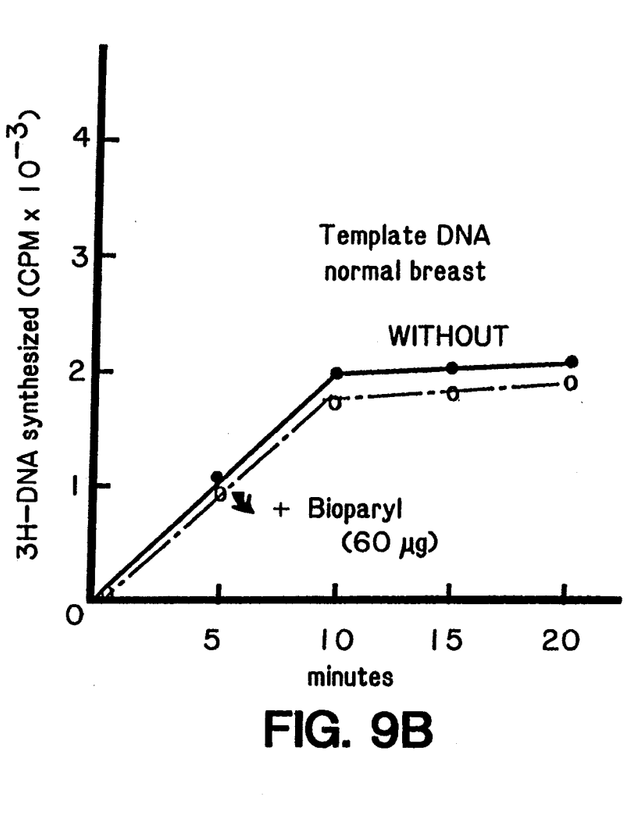
Figure 10:
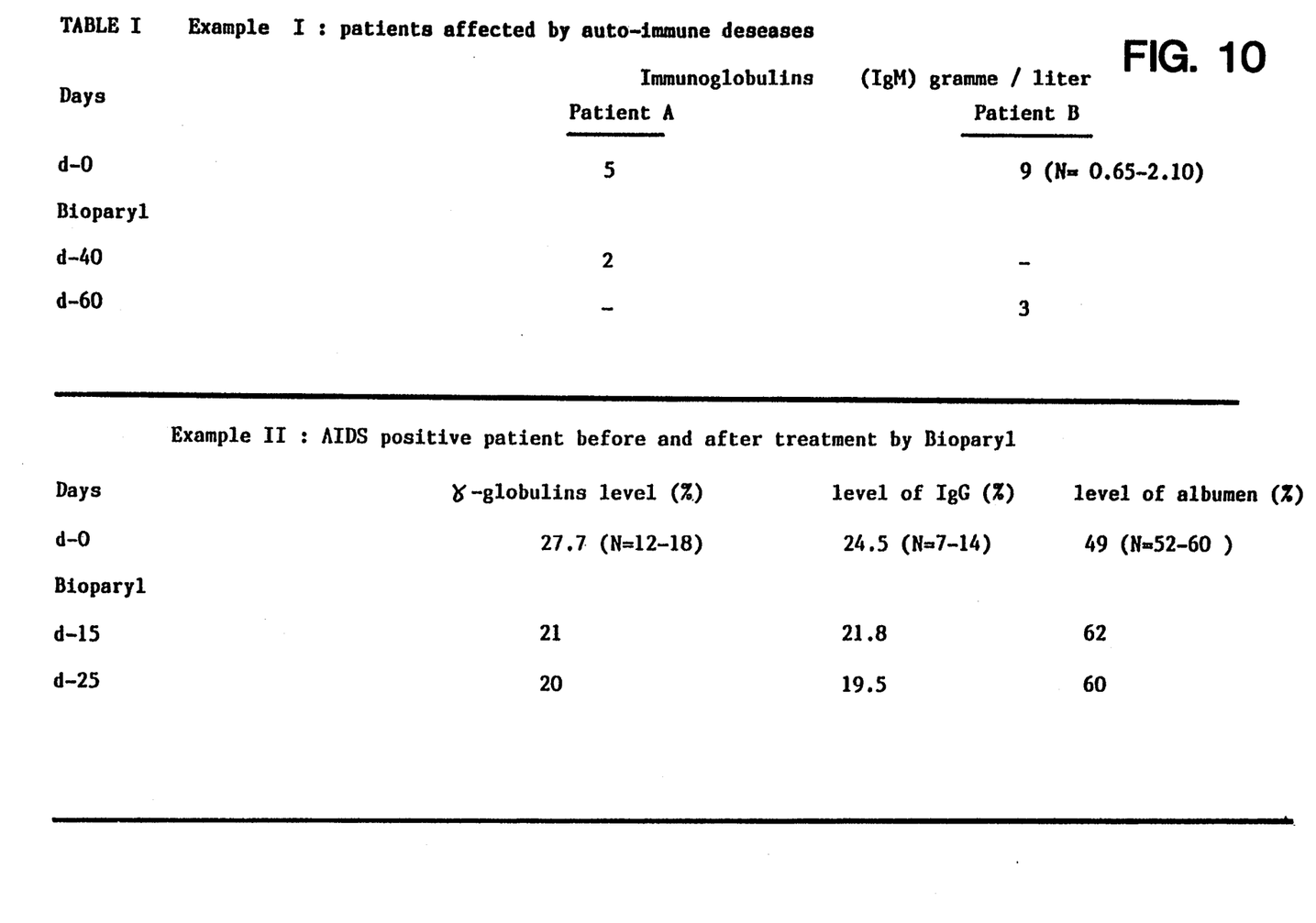
FIG. 10 is a Table I. Role of Bioparyl in normalizing the amount of gamma-globulins and immuno-globulins in two cases of auto-immune diseases and in a case of AIDS.

Under in vitro conditions, Bioparyl acts only on the synthesis of cancer cells DNA (human breast, ovary and lung cancer) without affecting, under the same conditions, that of normal DNA (breast, lung, spleen or bone marrow of humans). Initiation and elongation of cancer DNA formation are arrested by Bioparyl while those of normal DNA are not. FIG. 9. This may be demonstrated by introducing the Bioparyl either at start or after synthesis has been initiated, in the manner described in detail in my French patent application No. 88-08434, filed Jun. 23, 1988 (corresponding U.S. application Ser. No. 07/365,047, now U.S. Pat. No 5,145,839, filed on the same date as the present application, the disclosure of which is hereby incorporated herein by reference).

Figure 11:
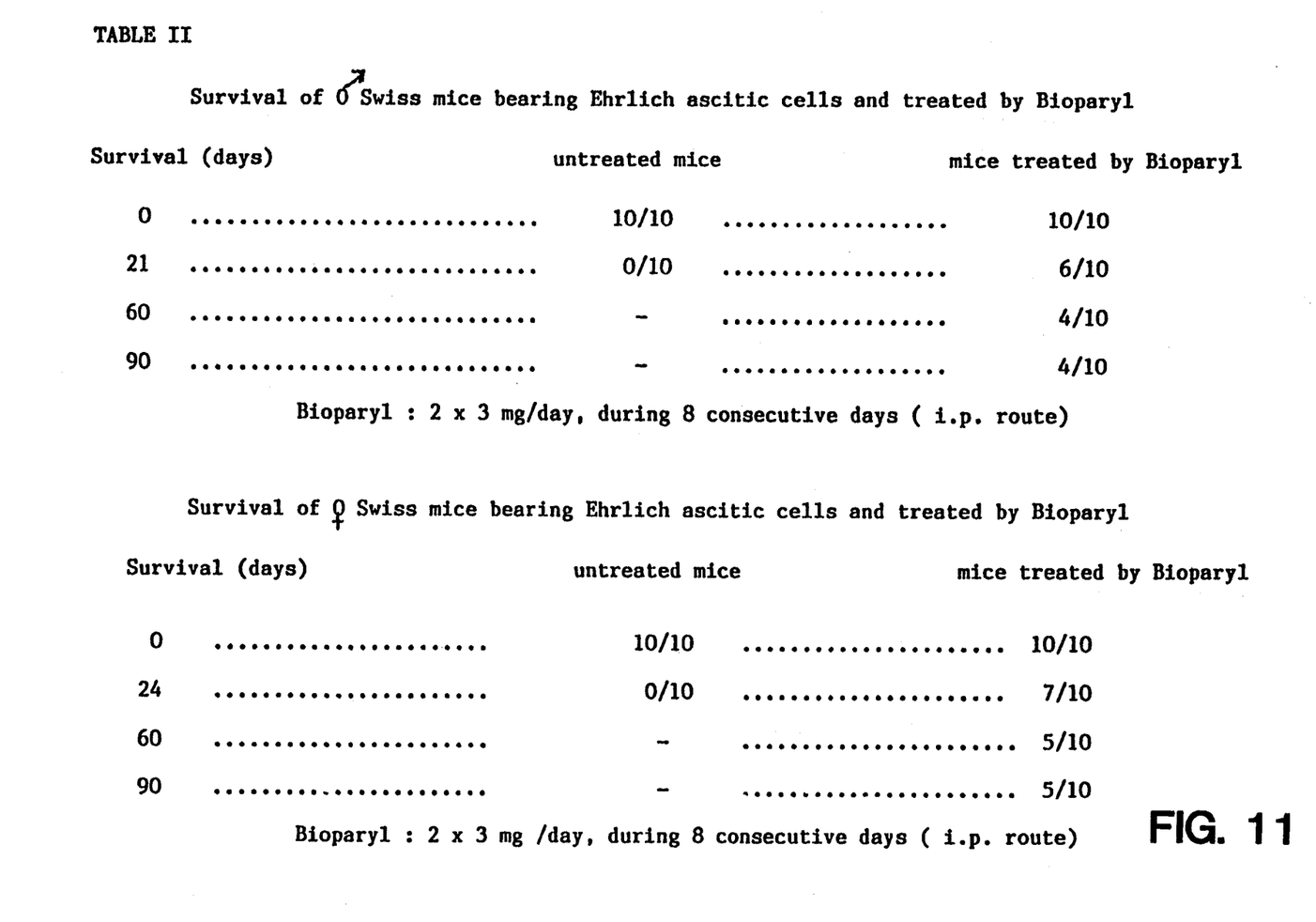
FIG. 11 is a Table II. Inhibition of the multiplication of cancer cells in mice under the effect of Bioparyl (Ehrlich ascitic cells).
Figure 12:
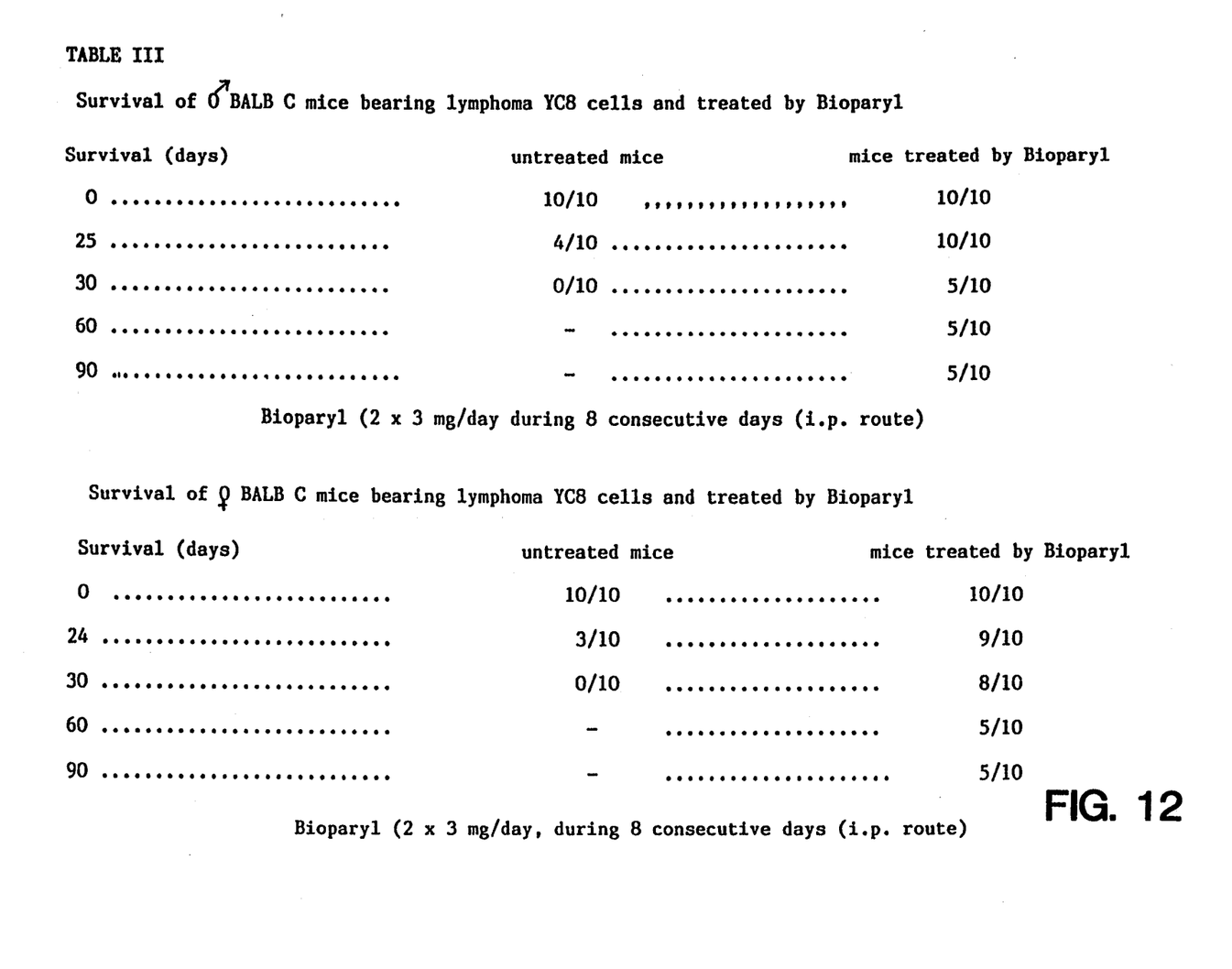
FIG. 12 is a Table III. Inhibition of the multiplication of cancer cells in mice under the effect of Bioparyl (lymphoma YC8).

In vivo with mice. 60 BALB C mice (30 ♂ and 30 ♀, 18 g each) bearing tumor cells (lymphoma YC8), and 60 CD1 Swiss mice (30 ♂ and 30 ♀) bearing tumor cells (Ehrlich ascites), (4,000-6,000 cells were injected by i.p. route 48 hours before the start of treatment) received Bioparyl twice per day (2×3 mg/day during 8 consecutive days, i.p.route). Control mice, instead of Bioparyl, received isotonic solution of NaCl. Results presented in Tables II and III reveal a certain anticancer activity of Bioparyl which, however, in humans and given per os, is not sufficient.

Toxicity and Posology

Acute toxicity of Bioparyl. Standardized Bioparyl preparation, administered orally at unique dosage to BALB C and Swiss mice as well as to rats, exhibited no toxic effect. In fact, LD50 in the case of mice is greater than 2,000 milligrams per kilogram. LD50 for rats is greater than 3,000 milligrams per kg.

Chronic toxicity. Administered orally at dosage of 2,000 milligrams per kg twice a week during three consecutive months, Bioparyl does not modify the behavior of mice which exhibit a normal increase in body weight and have unchanged prolificity and normal offspring. One dose of 1,000 milligrams per day (oral route, which corresponds to an active daily dose) during months is perfectly well tolerated by human beings.

Acute toxicity. Bioparyl by intraperitoneal and intravenous routes (BALB C and Swiss mice), LD50 is about 1,200 milligrams per kg and tolerated dose is 1,000 milligrams per kg. 250 milligrams/kg/day during 2 months are perfectly well tolerated, and mice development is completely normal. One dose of 250–800 milligrams/kg of Bioparyl injected by intravenous route to Swiss mice is perfectly tolerated. In humans, oral doses of 1,000–3,000 milligrams per day and during months are well tolerated. Intramuscular route can be planned at doses of 250–1,000 milligrams per day and by intravenous route 250 to 800 milligrams per day.

What is claimed:

1. A method of obtaining Bioparyl from golden autumn leaves of the *Gingko biloba* tree which comprises:
   (1) treating such leaves with water to obtain a water extract; removing the liquid extract from the leaves;
   (2) optionally concentrating the extract by evaporating part of the water;
   (3) subjecting the extract to acid hydrolysis;
   (4) adjusting the pH by partial neutralization retaining an acid pH;
   (5) centrifuging and recovering the supernatant;
   (6) subjecting the supernatant to column chromatography to eliminate undesirable substances by retention on the column, eluting solid material with water;
   (7) collecting eluate containing fractions that fluoresce under ultraviolet light; and
   (8) adjusting the pH to about 7.0 to obtain a water solution of Bioparyl.

2. A method according to claim 1 wherein in step (1) the leaves are treated with hot water.

3. A method according to claim 1 wherein in step (1) the leaves are treated with boiling water.

4. Bioparyl obtained in accordance with the method of claim 1.

5. A pharmaceutical composition comprising an admixture of Bioparyl according to claim 4 and a pharmaceutically acceptable carrier.

6. A unit dosage form containing the composition of claim 5.

7. The unit dosage of claim 6, said unit containing from 0.1 to 3 grams of Bioparyl.

* * * * *